United States Patent
Senanayake et al.

(10) Patent No.: US 6,822,099 B2
(45) Date of Patent: Nov. 23, 2004

(54) METHOD OF RESOLVING AMLODIPINE RACEMATE

(75) Inventors: Chris H. Senanayake, Danbury, CT (US); Gerald J. Tanoury, Hudson, MA (US); Harold S. Wilkinson, Marlborough, MA (US); Roger P. Bakale, Shrewsbury, MA (US); Andrei A. Zlota, Sharon, MA (US)

(73) Assignee: Sepracor, Inc., Marlborough, MA (US)

( * ) Notice: Subject to any disclaimer, the term of this patent is extended or adjusted under 35 U.S.C. 154(b) by 0 days.

(21) Appl. No.: 10/325,686

(22) Filed: Dec. 20, 2002

(65) Prior Publication Data

US 2003/0130321 A1 Jul. 10, 2003

Related U.S. Application Data

(63) Continuation-in-part of application No. PCT/US02/33894, filed on Oct. 23, 2002.
(60) Provisional application No. 60/346,250, filed on Oct. 24, 2001.

(51) Int. Cl.[7] .................. C07D 213/80; C07D 213/803
(52) U.S. Cl. ................. 546/355; 546/321; 546/319; 546/356

(58) Field of Search .................. 546/321, 319, 546/356, 355

(56) References Cited

U.S. PATENT DOCUMENTS

5,750,707 A * 5/1998 Spargo ............... 546/321
6,046,338 A * 4/2000 Spargo ............... 546/322
6,057,344 A   5/2000 Young

FOREIGN PATENT DOCUMENTS

| EP | 0 287 828 | 10/1988 |
| EP | 0 295 333 | 12/1988 |
| EP | 1 181 932 | 2/2002 |
| EP | 1 258 477 | 11/2002 |
| WO | WO 95/25722 | 9/1995 |
| WO | WO 01/60799 | 8/2001 |

* cited by examiner

*Primary Examiner*—Rita Desai
(74) *Attorney, Agent, or Firm*—Ropes & Gray LLP

(57) ABSTRACT

The invention relates to methods of resolving racemic amlodipine into enantiomerically enriched compositions by precipitation with tartaric acid in the presence of a non-aqueous solvent, such as N,N'-dimethylacetamide. The molar ratio of tartaric acid:amlodipine is preferably less than 0.25:1.0 or greater than 0.75:1.0.

14 Claims, No Drawings

METHOD OF RESOLVING AMLODIPINE RACEMATE

RELATED APPLICATIONS

This application is a continuation-in-part of International Application No. PCT/US02/33894, filed on Oct. 23, 2002, which claims the benefit of priority from U.S. Provisional Application Ser. No. 60/346,250, filed on Oct. 24, 2001, the specifications of which are incorporated by reference herein in their entirety. PCT Application PCT/US02/33894 was published under PCT Article 21(2) in English.

RELATED APPLICATIONS

This application is a continuation-in-part of PCT Application No. US02/33894, filed Oct. 23, 2002, in English, which claims priority to U.S. Provisional Application No. 60/346250, filed Oct. 24, 2001, the specifications of each of which are hereby incorporated by reference herein in their entirety.

FIELD OF THE INVENTION

The present invention relates to a method of resolving racemic amlodipine into its R-(+) and S-(−) enantiomers by precipitation with tartaric acid.

BACKGROUND OF THE INVENTION

The synthesis of racemic amlodipine (3-ethyl-5-methyl-2-(2-aminoethoxymethyl)-4-(2-chlorophenyl)-1,4-dihydro-6-methyl-3,5-pyridinedicarboxylate) and its activity as an inhibitor of calcium channels is described in U.S. Pat. No. 4,572,909 to Campbell et al. Results of in vitro tests to determine calcium antagonist activity of amlodipine enantiomers against calcium-induced constriction of potassium-depolarized rat aorta is described in Arrowsmith et al., *J. Med. Chem.*, (1986) 29, 1696–1702. The authors allege that the (−) stereoisomer is twice as active as the racemic mixture in antagonizing calcium-induced constriction. The S absolute configuration is the (−) optical rotatory form. Goldmann, *J. Med. Chem.*, (1992)35, 3341–44. Desirability of optically pure S-(−)-amlodipine for treatment of hypertension and angina is described in U.S. Pat. No. 6,057,344.

Although R-(+)-amlodipine appears to have little activity as a calcium channel blocker, it is not pharmacologically inert, but rather it is a potent inhibitor of smooth muscle cell migration. WO 95/05822 (now U.S. Pat. No. 6,080,761) to Chahwala et al. Ideally, the preferred mode of using amlodipine would be the administration of the S-(−) enantiomer substantially free of the R-(+) enantiomer. U.S. Pat. No. 6,057,344 to Young. Nonetheless, there is presently no amlodipine product that contains S-(−)-amlodipine substantially free of the R-(+) enantiomer. See, for example, NORVASC®, the active ingredient of which is racemic amlodipine besylate.

Methods of producing enantiomerically pure amlodipine have concentrated on methods of resolving the racemate, i.e., methods of separating the enantiomers of a racemic mixture of amlodipine or an intermediate in the synthesis of amlodipine by stereoselective precipitation. Such methods are known. See EP 331 315 A2 to Arrowsmith (resolution of an amlodipine intermediate by cinchonidine).

Spargo described a method of resolving racemic amlodipine by forming a precipitate in a dimethylsulfoxide (DMSO) solvent by addition of D- or L-tartaric acid. WO 95/25722 (now U.S. Pat. No. 6,046,338). The resultant precipitate consists of amlodipine:tartrate:DMSO in a 2:1:2 ratio, which is termed an amlodipine hemitartrate DMSO monosolvate.

Spargo optionally allowed for the presence of a co-solvent in an amount that is preferably between 0.2% and 6% the volume of DMSO. Suitable co-solvents are taught to include dimethylacetamide, dimethylformamide (DMF), acetonitrile and tetrahydrofuran (THF). Spargo further describes a method of secondarily processing the amlodipine hemitartrate DMSO monosolvate to obtain crystalline amlodipine free base by a process of extraction of the amlodipine hemitartrate DMSO monosolvate in dichloromethane (DCM) with aqueous NaOH to remove the tartrate followed by precipitation with hexane.

However, the use of DMSO renders the method of Spargo unsuitable for large-scale (kilogram) routine production of enantiomeric amlodipine. FDA guidelines point out that DMSO residual concentrations above 0.5% would only be acceptable upon convincing justification. *Guidance for Industry IMPURITIES: RESIDUAL SOLVENTS*, FDA, September 1999, page 9. Accordingly, there is an art-recognized need for commercially acceptable large-scale methods of resolving amlodipine.

SUMMARY OF THE INVENTION

In one aspect, the invention is directed to a method of optically enriching racemic amlodipine, comprising precipitating amlodipine hemitartrate dimethylacetamide monosolvate from a solution comprising amlodipine and either D- or L-tartaric acid, whereby the amlodipine hemitartrate dimethylacetamide monosolvate precipitate is enriched for one enantiomer of amlodipine. In certain embodiments, the ratio of the two enantiomers of amlodipine in the precipitate is at least 8:1, preferably at least 9:1, or even at least 20:1. In certain embodiments, the method includes heating a slurry or solution of amlodipine and tartaric acid, e.g., to a temperature above 35° C., preferably above 45° C. or even above 55° C., such as between 35 and 100° C., preferably between 50 and 90° C., even more preferably between 60 and 80° C. In certain such embodiments, the elevated temperature is maintained for at least 30 min., preferably at least 60 min. or even more than 2 hours. In certain embodiments, the resolution is performed on a scale of more than 1 kg of amlodipine, preferably at least 10 kg or even more than 100 kg of amlodipine.

In another aspect, the invention is directed to a crystalline composition comprising S-(−)-amlodipine D-hemitartrate DMAC monosolvate or, alternatively, R-(+)-amlodipine L-hemitartrate DMAC monosolvate, wherein at least 80% of the amlodipine in the crystalline composition is the predominant enantiomer. Preferably at least 90% of the amlodipine in the crystalline composition is the predominant enantiomer. More preferably at least 97% of the amlodipine in the crystalline composition is the predominant enantiomer. Most preferably at least 99% of the amlodipine in the crystalline composition is the predominant enantiomer.

In yet another embodiment, the invention is directed to solid pharmaceutical dosage forms comprising an optically active amlodipine or a pharmaceutically acceptable salt or hydrate thereof, and a carrier matrix, and to methods for manufacturing such dosage forms. In certain preferred embodiments, at least 80% of the optically active amlodipine in the dosage form is S-(−)-amlodipine, preferably at least 90%, or even 95% or more.

DETAILED DESCRIPTION OF THE INVENTION

The present invention is based on the discovery that the resolution of amlodipine by precipitation with D- or L-tartaric acid from N,N'-dimethylacetamide (hereinafter dimethylacetamide or DMAC) is suitable for the large scale production of enantiomerically enriched amlodipine.

The present invention encompasses the further discovery that a volatile, hydrophobic, non-chlorinated solvent such as methyl t-butyl ether (MTBE), ethyl acetate, toluene, or isopropyl acetate is useful in the secondary processing of the amlodipine hemitartrate DMAC monosolvate.

The present resolution method provides a solid (e.g., granular or powder) form of optically active amlodipine.

I. Process for Optically Enriching Racemic Amlodipine

In general, the subject method includes forming a precipitate of amlodipine hemitartrate dimethylacetamide monosolvate from a solution comprising amlodipine and either D- or L-tartaric acid, whereby the amlodipine hemitartrate dimethylacetamide monosolvate precipitate is enriched for one enantiomer of amlodipine. The enantiomer of amlodipine, or a pharmaceutically acceptable salt or free acid thereof, along with a pharmaceutically acceptable carrier can then be formed into a solid tablet.

A. Precipitation of the Amlodipine Hemitartrate DMAC Monosolvate

In one embodiment, the amlodipine hemitartrate DMAC monosolvate precipitate can be formed as follows. The absolute concentrations in this embodiment are merely exemplary, and can be varied as determined by routine experimentation. Racemic amlodipine free base is dissolved in a solvent comprising DMAC. The solvent comprises sufficient DMAC to induce crystallization of the DMAC solvate of amlodipine, e.g., at least 50% DMAC, preferably at least 80%, at least 90%, approximately 100% DMAC, or otherwise consisting essentially of DMAC, and may include amlodipine solute at a concentration of about 0.55 M, for example. If the starting material is an amlodipine acid addition salt, such as a besylate salt of amlodipine, the free base can be formed by any suitable technique as is well known in the art, such as extraction of an amlodipine salt suspension in MTBE (e.g., about 0.25 M) with aqueous NaOH, followed by concentration of the resultant free base by vacuum distillation. To the free base solution in the solvent, is added D- or L-tartaric acid. The tartaric acid may be added as a solid or, preferably, as a solution in either DMAC, the solvent used to dissolve the amlodipine, or any other suitable solvent, optionally at a concentration of about 0.55 M. D-Tartaric acid is used to precipitate S-(−)-amlodipine as the S-(−)-amlodipine D-hemitartrate DMAC monosolvate and L-tartaric acid precipitates R-(+)-amlodipine as the R-(+)-amlodipine L-hemitartrate DMAC monosolvate. The ratio of tartaric acid to racemic amlodipine is preferably less than about 0.3 mol tartaric acid per mol racemic amlodipine or greater than about 0.7 mol tartaric acid per mol racemic amlodipine.

The mixture may be stirred, e.g., for between 3 and 5 hours at room temperature or a temperature up to 100° C., e.g., between 60 and 80° C., preferably 70° C., as the amlodipine salt crystallizes from the solution during cooling, and the resultant crystals may be filter-separated from the solution, preferably at room temperature. In embodiments including temperatures higher than room temperature, the elevated temperature may be maintained for at least 15 or 30 min., preferably at least about an hour, or even 2–3 hours or more. The resulting crystals may be washed, e.g., successively with DMAC and MTBE, dried in vacuo, weighed, and assayed for optical purity. The above process is amenable to large-scale (1 kilogram and greater) resolution of amlodipine, and the elevated temperature is especially beneficial in large-scale resolutions.

When practicing the method of the invention, a yield of about 80% of theoretical may be achieved with 99.5% enantiomeric purity. Those skilled in the art will appreciate that resolutions in which the enantiomeric purity is as low as 80% can be useful; however, enantiomeric purities of 90% or 99% are desirable.

Excellent results in performing the above method can be obtained using a 1:1 molar ratio in DMAC. When the ratio of tartaric acid to amlodipine is either low, e.g., 0.25 mol or less tartaric acid per mol amlodipine, or high, e.g., 0.75 or more mol tartaric acid per mol amlodipine, the racemic amlodipine is resolved with good to excellent optical specificity, e.g., providing at least 90% enantiomeric excess. However, when the ratio of tartaric acid to amlodipine is between 0.25–0.75:1.0, the racemic mixture is typically less well resolved. For example, the use of a tartaric acid:amlodipine ratio of 0.5:1.0 resulted in less than 80% enantiomeric purity.

While not wishing to be bound by any theory, the above-described results could arise because the hemitartrates of both enantiomers are insoluble and thus precipitate, while the monotartrate of one enantiomer is highly soluble and the monotartrate of the other enantiomer does not form to any appreciable extent. Equilibration of the salt mixtures at temperatures greater than room temperature, e.g., between 60 and 80° C., preferably 70° C., provides enhanced opportunity for dissolution, equilibration and eventual preferred crystallization of the desired salt form containing amlodipine with at least 90% enantiomeric excess.

B. Precipitation of Enantiomeric Amlodipine Free Base

Enantiomeric amlodipine free base can be obtained from the enriched amlodipine hemitartrate DMAC monosolvate by a process of suspension in a substantially water-immiscible solvent, washed with aqueous NaOH, and precipitation by addition of a highly non-polar solvent, such as a hydrocarbon solvent, preferably an aliphatic hydrocarbon solvent.

In one exemplary embodiment, the enriched amlodipine hemitartrate DMAC monosolvate is suspended in MTBE at a concentration of about 0.15 M, and is successively extracted with 0.2 volumes aqueous NaOH and 0.2 volumes of water. The solution is then concentrated about three-fold by vacuum distillation and the precipitation of the product completed by addition of an equal volume of n-heptane. Other suitable solvents that can be used in place of or in addition to MTBE include ethyl acetate, toluene, xylene, isopropyl acetate, and the like, or any combination of two or more such solvents. Other suitable basic aqueous solutions, e.g., having a pH above 8, preferably above 9, or even above 10, can be employed in place of the NaOH solution, as will be understood by those skilled in the art. Other suitable solvents that can be used to facilitate precipitation of amlodipine free base include n-hexane and n-octane, as well as solvent mixtures such as ligroin, petroleum ether, and the like.

In certain embodiments, the above procedure provides a yield of about 85% of theoretical with an enantiomeric purity of the amlodipine of greater than 99.9%.

This procedure can also be employed for generating the free base from salts of amlodipine other than amlodipine hemitartrate DMAC monosolvate, such as amlodipine besylate, as will be understood by those skilled in the art. In certain such embodiments, the amlodipine salt is an acid addition salt of amlodipine and a chiral acid enriched to at least 90% enantiomeric excess.

C. Solid Dosage Forms

Formulations of optically active amlodipine suitable for oral administration may be in the form of capsules, cachets, pills, tablets, and the like, each containing a predetermined amount of amlodipine as an active ingredient.

In solid dosage forms for oral administration (capsules, tablets, pills, and the like), the optically active amlodipine is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as capsules, pills, and the like, may optionally be scored or prepared with coatings and shells, such as enteric coatings and other coatings well known in the pharmaceutical-formulating art. They may also be formulated so as to provide slow or controlled release of the amlodipine therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the amlodipine only, or preferentially, in a certain portion of the gastrointestinal tract, optionally, in a delayed manner. Examples of embedding compositions that can be used include polymeric substances and waxes. The amlodipine can also be in microencapsulated form, if appropriate, with one or more of the above-described excipients.

Besides inert diluents, the oral compositions can also include adjuvants such as wetting agents, emulsifying and suspending agents, sweetening, flavoring, coloring, perfuming and preservative agents.

Additional information relating to solid dosage forms of amlodipine can be found in U.S. Pat. Nos. 4,879,303, 5,178,867, and 6,057,344.

Exemplification

The invention now being generally described, it will be more readily understood by reference to the following examples, which are included merely for purposes of illustration of certain aspects and embodiments of the present invention, and are not intended to limit the invention.

EXAMPLE 1
S-(−)-amlodipine D-hemitartrate DMAC Monosolvate

Aqueous sodium hydroxide (1 N, 530 mL) was added to a stirred suspension of amlodipine besylate (200 g, 0.353 moles) in methyl t-butyl ether (1.3 L). The reaction mixture was stirred for 20–30 minutes after which the aqueous and organic layers were allowed to separate. After removing the aqueous layer, water (220 mL) was added to the organic layer and the mixture was stirred for 20 minutes. The aqueous layer was again removed and the organic layer was concentrated to approximately one-third of its original volume by vacuum distillation. The organic layer was collected and concentrated to approximately one-third of its original volume by distillation. The concentrate was then mixed with N,N-dimethylacetamide (DMAC, 650 ml) and further concentrated by vacuum distillation until the temperature of the concentrate rose by 10–15° C. The concentrate was allowed to equilibrate to room temperature and pressure before it was added to a stirred solution of D-tartaric acid (55.12 g, 0.367 mol) in N,N-dimethylacetamide (650 mL). The resulting slurry was stirred for 3–5 hr followed by filtration. After the residual crystalline solid was washed successively with dimethylacetamide (650 mL) and methyl t-butyl ether (650 mL), it was dried in vacuo at 40–50° C. for 8–16 hr to yield, S-(−)-amlodipine D-hemitartrate DMAC monosolvate (85.5 g, 41% yield, 98.98% enantiomeric purity, >99% chemical purity).

EXAMPLE 2
S-(−)-amlodipine Free Base

Aqueous sodium hydroxide (1 N, 220 mL) was added to a stirred suspension of S-(−)-amlodipine D-hemitartrate DMAC monosolvate (81.1 g, 0.142 moles) in methyl t-butyl ether (960 mL). The reaction mixture was stirred for 20–30 minutes after which the aqueous and organic layers were allowed to separate. After removing the aqueous layer, water (220 mL) was added to the organic layer and the mixture was stirred for 20 minutes. The aqueous layer was again removed and the organic layer was concentrated to approximately one-third of its original volume by vacuum distillation. After allowing the concentrate to equilibrate to room temperature and pressure, heptane (320 mL) was added and the resulting slurry was stirred for 1–2 hr. The slurry was then filtered, and the residual crystalline solid was washed with heptane (500 mL). The crystals were dried in vacuo at 40–50° C. for 8–16 h to yield S-(−)-amlodipine free base (49.10 g, 85% yield, 99.96% enantiomeric purity, >99% chemical purity).

EXAMPLE 3
S-(−)-amlodipine D-hemitartrate DMAC Monosolvate (RS)-amlodipine (24.85 kg, 60.8 moles) and N,N-dimethylacetamide (DMAC, 104 kg) are added to a reactor and stirred at 20 to 25° C. for 15 to 30 minutes. A solution of D-tartaric acid (9.5 kg, 63.2 mol) in N,N-dimethylacetamide (104 kg) is added at 20 to 25° C. The mixture is heated to 68 to 70° C. over about 60 minutes and stirred for about 60 minutes. The solution is cooled to 20 to 23° C. over 2 to 3 hr and the slurry is then held for about 30 to 45 minutes at 20 to 23° C. The slurry is then filtered and the residual crystalline solid is washed successively with N,N-dimethylacetamide (about 50 kg) and methyl t-butyl ether (about 40 kg). The filter cake is dried in vacuo at 40 to 50° C. for 8 to 16 hr to yield, S-(−)-amlodipine D-hemitartrate DMAC monosolvate (14 kg, 40% yield, 99.2% enantiomeric purity, >99% chemical purity).

EXAMPLE 4

S-(−)-amlodipine Free Base

Aqueous sodium hydroxide (75.8 kg, 1 N) is added to a stirred suspension of S-(−)-amlodipine D-hemitartrate DMAC monosolvate (26.9 kg, 47.4 moles) in methyl t-butyl ether (220 kg). The reaction mixture is stirred for 20 to 30 minutes after which the aqueous and organic layers are allowed to separate. After removing the aqueous layer, water (73 kg) is added to the organic layer and the mixture is stirred for 20 to 30 minutes. The aqueous layer is removed and organic layer is washed with water again (total 2×73 kg water). The organic layer is concentrated to approximately one-third of its original volume (~85 L) by vacuum distillation. After allowing the concentrate to equilibrate to room temperature and pressure, heptane (73 kg) is added over 45 to 60 minutes and the resulting slurry is stirred for about 1 hr. The slurry is then filtered, and the residual crystalline solid is washed with heptane (118 kg). The filter cake is dried in vacuo at 40 to 50° C. for 8 to 16 hr to yield S-(−)-amlodipine free base (17.7 kg, 91.7% yield, 99.98% enantiomeric purity, >99.5% chemical purity).

Those skilled in the art will recognize, or be able to ascertain using no more than routine experimentation, many equivalents to the specific embodiments of the invention described herein. Such equivalents are intended to be encompassed by the following claims.

All references, publications and patents cited in the specification above are herein incorporated by reference.

What is claimed is:

1. A method of optically enriching racemic amlodipine, comprising precipitating amlodipine hemitartrate dimethylacetamide monosolvate from a solution comprising amlodipine, dimethylacetamide, and either D- or L-tartaric acid, whereby the amlodipine hemitartrate dimethylacetamide monosolvate precipitate is enriched for one enantiomer of amlodipine.

2. The method of claim 1, wherein amlodipine and D- or L-tartaric acid are initially present in the solution in a ratio of less than 0.3 moles tartaric acid per mole of amlodipine.

3. The method of claim 1, wherein amlodipine and D- or L-tartaric acid are initially present in the solution in a ratio of greater than 0.7 moles tartaric acid per mole of amlodipine.

4. The method of claim 1, wherein amlodipine and D- or L-tartaric acid are initially present in the solution in approximately equal molar amounts.

5. The method of claim 1, wherein the amlodipine hemitartrate dimethylacetamide monosolvate is enriched for S-(−)-amlodipine D-hemitartrate dimethylacetamide monosolvate.

6. The method of claim 1, wherein the solvent in which the amlodipine and tartaric acid are dissolved consists essentially of dimethylacetamide.

7. The method of claim 1, further comprising treating the amlodipine hemitartrate dimethylacetamide monosolvate with an aqueous solution having a pH of at least 8 to convert the amlodipine hemitartrate dimethylacetamide to amlodipine free base.

8. The method of claim 7, wherein converting the precipitate to amlodipine free base is accomplished by:

a. suspending the precipitate in an organic solvent consisting essentially of methyl tert-butyl ether, ethyl acetate, toluene, isopropyl acetate, or any combination thereof;

b. contacting the suspension with a basic aqueous solution to extract the tartrate ions into the aqueous solution; and c. precipitating amlodipine free base from the organic solvent by reduction of the volume of organic solvent and addition of a non-polar organic solvent.

9. The method of claim 8, wherein the non-polar organic solvent comprises an aliphatic hydrocarbon solvent.

10. The method of claim 9, wherein the aliphatic hydrocarbon solvent is selected from n-hexane, n-heptane, and n-octane.

11. The method of claim 1, wherein the solution is heated to at least 50° C. prior to precipitating the precipitate.

12. The method of claim 1, wherein the solution is heated to at least 60° C. prior to precipitating the precipitate.

13. The method of claim 11, wherein the temperature of the solution is maintained above 50° C. for at least 30 minutes.

14. The method of claim 12, wherein the solution is heated to at least 60° C. for at least 30 minutes.

* * * * *